(12) United States Patent
Villard et al.

(10) Patent No.: US 9,687,179 B2
(45) Date of Patent: Jun. 27, 2017

(54) SYSTEM AND METHOD TO RECOGNIZE ACTIVITIES PERFORMED BY AN INDIVIDUAL

(71) Applicant: WITHINGS, Issy les Moulineaux (FR)

(72) Inventors: Joffrey Villard, Paris (FR); Pierre Duquesne, Paris (FR); Paul Edouard, Fontenay (FR); Cedric Hutchings, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 42 days.

(21) Appl. No.: 14/668,616

(22) Filed: Mar. 25, 2015

(65) Prior Publication Data
US 2016/0278667 A1    Sep. 29, 2016

(51) Int. Cl.
| | |
|---|---|
| *A61B 5/11* | (2006.01) |
| *G01C 22/00* | (2006.01) |
| *G06F 19/00* | (2011.01) |

(52) U.S. Cl.
CPC .......... *A61B 5/1118* (2013.01); *G01C 22/006* (2013.01); *G06F 19/3481* (2013.01)

(58) Field of Classification Search
None
See application file for complete search history.

(56) References Cited

U.S. PATENT DOCUMENTS

| | | | | |
|---|---|---|---|---|
| 2006/0284979 A1* | 12/2006 | Clarkson | ................ | A61B 5/061 348/143 |
| 2014/0257535 A1 | 9/2014 | Morris et al. | | |
| 2014/0278139 A1* | 9/2014 | Hong | ................... | A61B 5/4866 702/19 |
| 2015/0201867 A1* | 7/2015 | Peindl | ................... | A61B 5/1118 600/595 |
| 2015/0289822 A1* | 10/2015 | Dugan | ................. | A61B 5/0077 600/301 |

* cited by examiner

*Primary Examiner* — Robert R Raevis
(74) *Attorney, Agent, or Firm* — Miller, Matthias & Hull LLP

(57) ABSTRACT

A method implemented in a system which comprises a lightweight personal wearable monitoring device, supplied by a battery, comprising an accelerometer, a processing unit, a display, a remote server, said method comprising the steps:
/a/ collecting, from a plurality of individuals caused to practice various physical activities from a set of predefined activities, acceleration data from sensing devices placed on each of said individuals,
/b/ defining N small data-size specific metrics, computed from acceleration signals, which allow to define a global activity classifier,
/c/ acquiring, at a first monitoring device worn by a first user, acceleration signals from the accelerometer of the first monitoring device,
/d/ calculating, at the first monitoring device, over each lapsed time unit T1, specific metrics values from the sensed signals, to form a series of specific metrics values,
/e/ send them to the processing unit,
/f/ allocate an activity type for each time unit together with corresponding specific metrics values of the received series, to form a time chart of activity types presumably performed by the first user over a second period T2,
/g/ display the time chart of activity types presumably performed by the first user on the display and allow the first user to confirm or correct partly the type of activity performed over the second period, and allow correction by the first user.

12 Claims, 4 Drawing Sheets

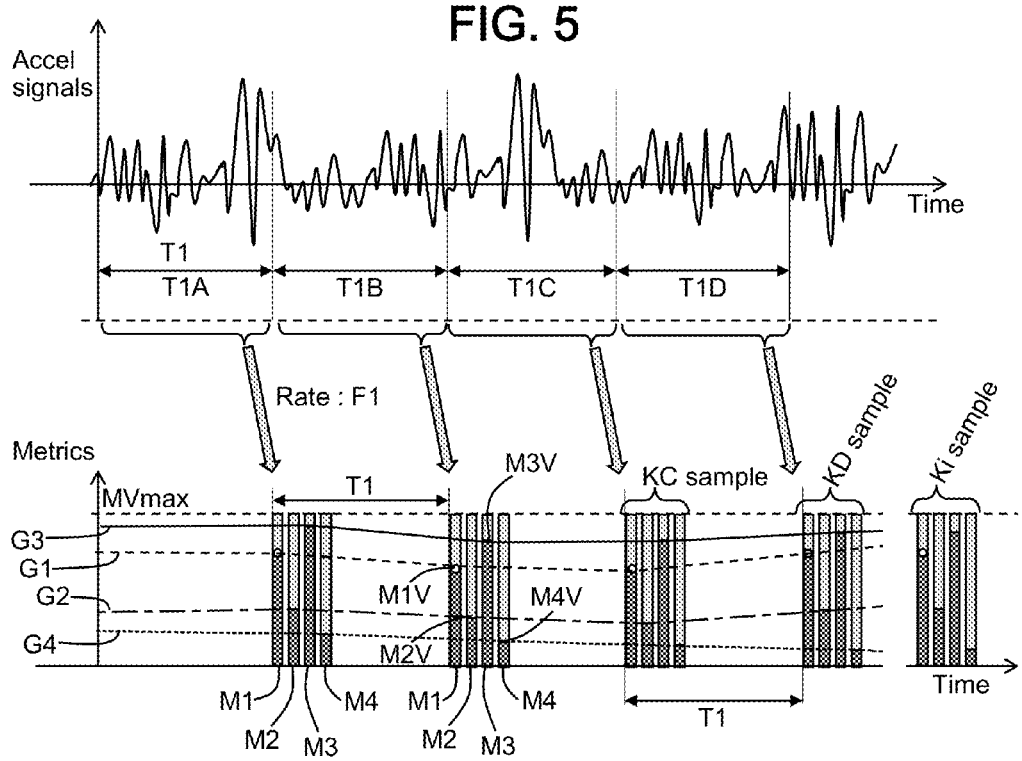
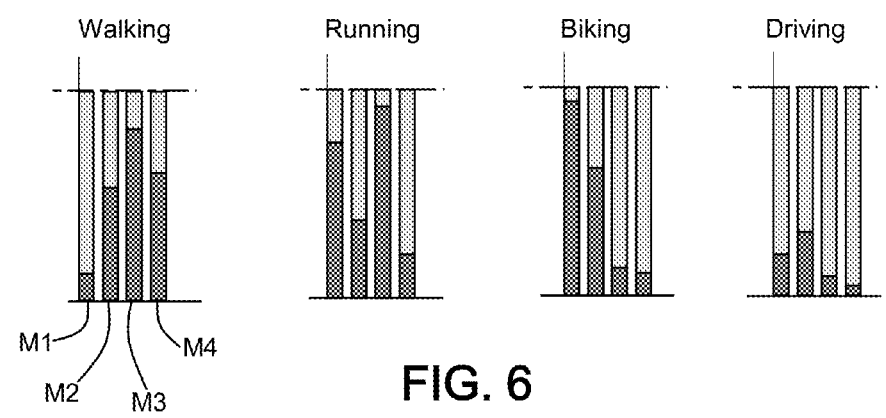

SYSTEM AND METHOD TO RECOGNIZE ACTIVITIES PERFORMED BY AN INDIVIDUAL

FIELD OF THE DISCLOSURE

This disclosure relates to systems and methods to recognize activities performed by an individual, particularly various physical activities.

BACKGROUND OF THE DISCLOSURE

More precisely, this disclosure relates to a monitoring system and to a monitoring method, which allows to identify activities undertaken by an individual (the 'user'), and further give personalized advice and coaching to the individual about his/her health.

It is known from US20140278139 or US20140257535 to have a monitoring device intended to be worn by the user and configured to recognize activities undertaken by this individual. This kind of monitoring device is supplied by a battery, which requires to be recharged periodically.

However, it turns out that an accurate recognition requires significant computing power and this is therefore detrimental to the autonomy of the battery. Consequently, in the prior art, the user of such monitoring device has to recharge the battery rather frequently.

Therefore, there is a need to propose a lightweight small-size monitoring device which allows to recognize accurately the activities undertaken by the user, and also exhibits a very low electrical consumption and therefore favours a good battery autonomy.

SUMMARY OF THE DISCLOSURE

To this aim, according to this disclosure, there is provided a method a method implemented in a system which comprises:
- at least a lightweight personal wearable monitoring device, supplied by a battery, comprising at least an accelerometer which senses acceleration signals,
- a processing unit, a display,
- at least a remote server, said method comprising the steps:
/a/ collecting, from a plurality of individuals caused to practice various physical activities from a set of predefined activities, acceleration data from one or several sensing devices placed on each of said individuals, and at different body positions,
/b/ defining N small data-size specific metrics, to be computed from acceleration signals sensed by accelerometer(s) of monitoring devices, which allow to define a global activity classifier,
/c/ acquiring, over time, at a first monitoring device worn by a first user, acceleration signals from the accelerometer of the first monitoring device,
/d/ calculating, at the first monitoring device, periodically at a predefined rate F1, and over each lapsed time unit T1=1/F1, specific metrics values from the sensed signals, to form a series of specific metrics values,
/e/ send this series of specific metrics values to the processing unit,
/f/ at the processing unit 2, allocate an activity type for each time unit together with corresponding specific metrics values of the received series, to form a time chart of activity types presumably performed by the first user over a second period,
/g/ display the time chart of activity types presumably performed by the first user on the display and allow the first user to confirm or correct partly the type of activity performed over the second period,
/h/ if correction was stated by the first user, send a correction information back to the server, which allows to define or refine a user-specific activity classifier.

Therefore, thanks to the system and method, the user can wear a lightweight small monitoring device which accurately recognises activities and has a very low electrical power consumption.

Thanks to these dispositions, relevant specific metrics are determined, which allows the personal monitoring device to have simple computing operations to perform and results of metrics sent out, while the complicated task of activity classification is performed remotely at the processing unit; therefore, the personal monitoring device can have low computing power, low memory space, low electrical energy requirement, and low battery capacity (e.g. <200 mAh, even <100 mAh, even <50 mAh) with still a good battery autonomy (e.g. typically 2 weeks);

Further, the personal wearable monitoring device can be very small and lightweight; according to one example, weight of the device may be less than 10 g, preferably less than 8 g, even more preferably less than 7 g; dimensions can be less than 30 mm×20 mm×4 mm. The complex activity classifier is managed outside the wearable device, namely in the processing unit and/or in the remote server. The learning phase (step a/ and /b/) allows to define metrics and classifier that result in accurate activity recognition.

In various embodiments of this disclosure, one may possibly have recourse in addition to one and/or other of the following arrangements.

The set of predefined activities can comprise at least: normal walk, fast walk, run, dance, climbing stairs, rest, office sit, TV watch, sports like football, rowing, treadmill run, biking, skiing, skating). Whereby a wide variety of activities can be recognized, a complete and competency activities tracking can be performed.

The number of specific metrics N can be no greater than 8, wherein each metric has a size no greater than 8 Bits. Thereby achieving small size of data generated for each metric, and also for the whole set of metrics.

The number of specific metrics N can be equal to 5, wherein each metric has a size less than 5 Bits. Thereby achieving an even smaller size of data generated for each metric, and for the whole set of metrics.

Each metric can be computed at an end of every predefined time unit (T1) with the acceleration data sensed over the lapsed predefined time unit, said time unit having a duration comprised between 10 seconds and 360 seconds; thereby, a long period can be partitioned in 'slices' of time each being handled separately. Each time unit can also be time stamped.

The processing unit and the display preferably form part of a smartphone. This is a very common and popular user device, most people have one nowadays.

At step /f/, at the processing unit, the allocation of type activity relies on a transfer matrix computation. This forms a simple competition, preferably with only multiplications and additions.

At step /f/, at the processing unit, the allocation of type activity relies on the classifier resulting from the global classifier and the user-specific activity classifier, incrementally amended through parameterization with the user feedbacks. The activity classifier can thereby be rendered specific to a particular user.

The activity monitoring device can have a low battery capacity, namely less than 100 mAh and a good battery autonomy namely no less than 2 weeks.

BRIEF DESCRIPTION OF THE DRAWINGS

Other characteristics and advantages of this disclosure will readily appear from the following description of one of its embodiments, provided as a non-limitative example, and of the accompanying drawings.

FIG. 5 illustrates the process to compute specific metrics, FIG. 6 illustrates various metrics distribution or profile that are used during part of the process of classification.

DETAILED DESCRIPTION

Figure 1:
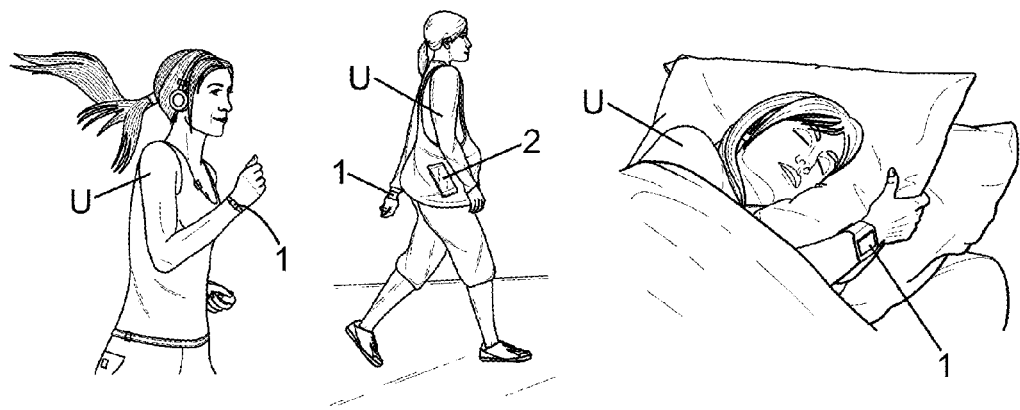
FIG. 1 illustrates various activities undertaken by an individual user.

FIG. 1 shows a user U (also called "individual" in the following) in various everyday life activities, namely as illustrated running, walking and sleeping. Everyday life usually involves many types of activities, and also some activities like practising sports can be divided or classified in a more refined classification: standard jogging, fast running, gymnastics, biking, tennis, squash, ski, rowing, swimming, paddling, dancing, etc. . . .

According to the present disclosure, the user wears an activity monitoring device 1, worn at the wrist in the shown example. However, such an activity monitoring device 1 can be worn elsewhere, close to the body of the user, at the ankle, at the waist, at the neck, or even in a cloth or a shoe. Such an activity monitoring is configured to sense accelerations, and therefore can basically assess the type of activity undertaken by the user or at least the level of activity.

There is defined a set of predefined activities which comprises at least the following: normal walk, fast walk, run, dance, climbing stairs, rest, office sit, TV watch, sports like football, rowing, treadmill run, biking, skiing, rowing, swimming, paddling, playing golf, skating, etc.

In order to accurately assess the caloric burn, some activities need to be finely classified, like for example, regarding walking: walking upstairs, walking downstairs, regarding running: running uphill, running downhill, regarding dancing:zumba dancing, classic dancing, modern dancing.

Also other types of activities may also be taken into account like car driving, sitting, standing in public transportation, plane taking, . . . .

However, it may be troublesome to distinguish between some activities, especially if the body position of the monitoring device is not known. Therefore, the monitoring device may not be able to recognise each activity, especially with the body position unknown.

According to this disclosure, the tricky task of accurately determining the activity undertaken by the user is not allocated to the monitoring device itself alone. Two other entities are involved as explained below.

Figure 2:
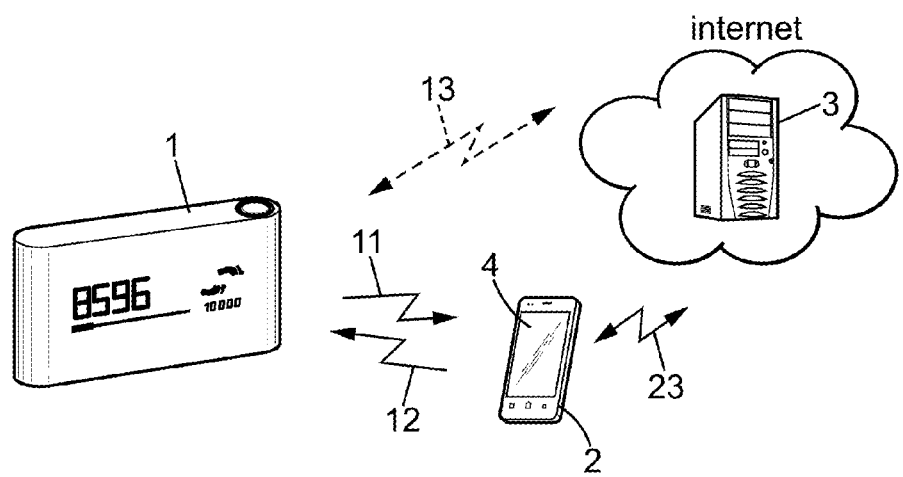
FIG. 2 shows an example of system in which the method according to this disclosure can be carried out.
Figure 3:
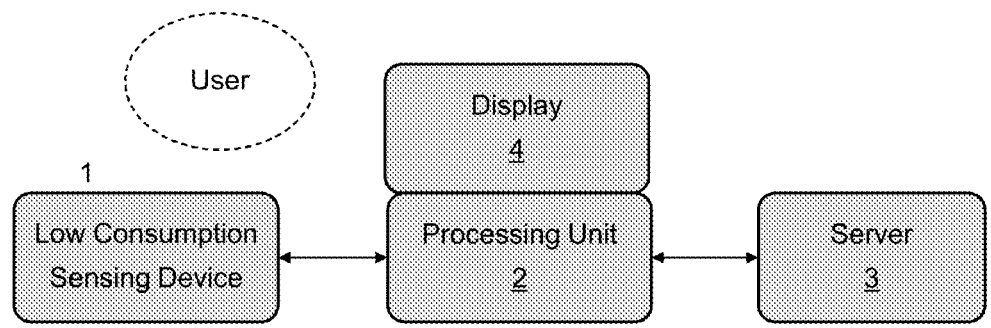
FIG. 3 shows the generic block diagram.

As shown in FIGS. 2 & 3, a processing unit 2 is provided. In the example shown, the processing unit 2 is embodied in the form of a smartphone. Said smartphone comprises a display 4, on which various information can be displayed.

However, in other embodiments, the display 4 could be located elsewhere than integrated with the processing unit, for example in another device, not excluding the monitoring device itself, smart glasses, or the like.

Likewise, the processing unit 2 can be something else apart from the smartphone, for example a PDA, a tablet, a phablet, or the like.

The activity monitoring device 1 can transmit data to the smartphone 2 via a wireless uplink 11 (Bluetooth™, or the like, preferably Bluetooth™ low energy). Likewise, the smartphone 2 can send data 12 to the activity monitoring device.

Further a remote server 3 is provided. In the example shown, the remote server 3 is embodied in the form of a conventional server that can be found in data centers. However, in other embodiments, the remote server is not a single device but a distributed resource in a cloud computing architecture.

The smartphone 2 and the remote server 3 can be in wireless communication 23 through Wifi and/or internet as known per se. Though, it is not excluding to have a direct communication 13 between the monitoring device 1 and the remote server 3.

Advantageously, the activity monitoring device 1 has a low battery capacity (e.g. generally less than 200 mAh, typically less than 100 mAh, preferably less than 75 mAh, even more preferably less than 50 mAh) with still a good battery autonomy (e.g. typically 2 weeks); this outstanding combination is achieved because the activity monitoring device 1 exhibits low computing power, low memory space, and therefore low electrical energy requirement.

The personal wearable monitoring device 1 can be very small-size and light-weight; according to one example, its weight may be less than 10 grams, preferably less than 8 g, even more preferably less than 7 g; dimensions can be less than 30 mm×20 mm×4 mm.

The monitoring device can also comprise a gyrometer, a pressure sensor, a temperature sensor or any other sensing device with small energy consumption.

The monitoring device is preferably deprived of GPS location device, which represents a high energy consumer.

It should be understood that the method disclosed here can work if the monitoring device as only an accelerometer and no other sensor(s).

The below-detailed advantageous process relies on metrics and classifiers which are defined according to an initial learning phase and they then may be refined incrementally later in relation with actual data coming from user(s) monitoring devices.

The initial learning phase comprises the following steps.

The first step /a/ consists in collecting, from a plurality of individuals caused to practice various physical activities taken from a set of predefined activities, acceleration data from one or several sensing devices placed on each of said individuals, and at different body positions.

More precisely, each individual of a group of voluntary individuals is equipped with a monitoring device or several monitoring devices at different body positions, and then each individual is instructed to practice sequentially a variety of physical activities, preferably every physical activity of the set of predefined activities. The recorded data is then uploaded and stored together with the associated body position and specific activity undertaken according to instructions. This forms a reference database of activities with associated acceleration signals.

In the shown example, there is defined from the reference database of acceleration signals, N=4 specific metrics.

It should be noted that the number of specific metrics N can be different from 4, in particular it can be N=5; it can also be 6, 7, 8 or more.

The N specific metrics give values which, taken as a set of values, are somehow representative of the type of activity of the user and location of the device on user's body.

An activity classifier, which will be detailed later below, allows to determine the most likely activity corresponding to the values of the N specific metrics.

Therefore, the second step of the phase can also be summarised as follows:

/b/ defining N specific metrics, to be computed from acceleration signals sensed by accelerometer(s) of monitoring devices, which allow to define a global activity classifier. This global activity classifier can be worked out at the server 3 or at any computer, it may particularly be the computer where the reference database of activities with associated acceleration signals is stored.

Up to that point, the global activity classifier reflects the data acquired with a large group of voluntary individuals, but is not specific to a particular user.

After the above described initial learning phase, the metrics and classifier are used for each monitoring device 1 worn by 'public' users. Public users is a large group of people that is normally different from the group of voluntary individuals discussed above for the learning phase; each 'public' user U of interest possesses a monitoring device 1. Each 'public' user U wears the monitoring device 1 at one particular body position, without excluding that the user may change from one position to another from time to time or according to the activity performed. The group of 'public' users is increasing with time and is likely to become much larger than the group of voluntary individuals discussed above for the learning phase. Also a 'public' user can practice an activity that was not part of the initial set of activities. Anyhow the group of voluntary individuals (discussed above for the learning phase) is chosen to be representative of the most popular activities undertaken generally by people.

In the monitoring device 1 worn by each user U, each specific metric comprises a digital filter applied on the sensed acceleration timed signals.

Figure 4:
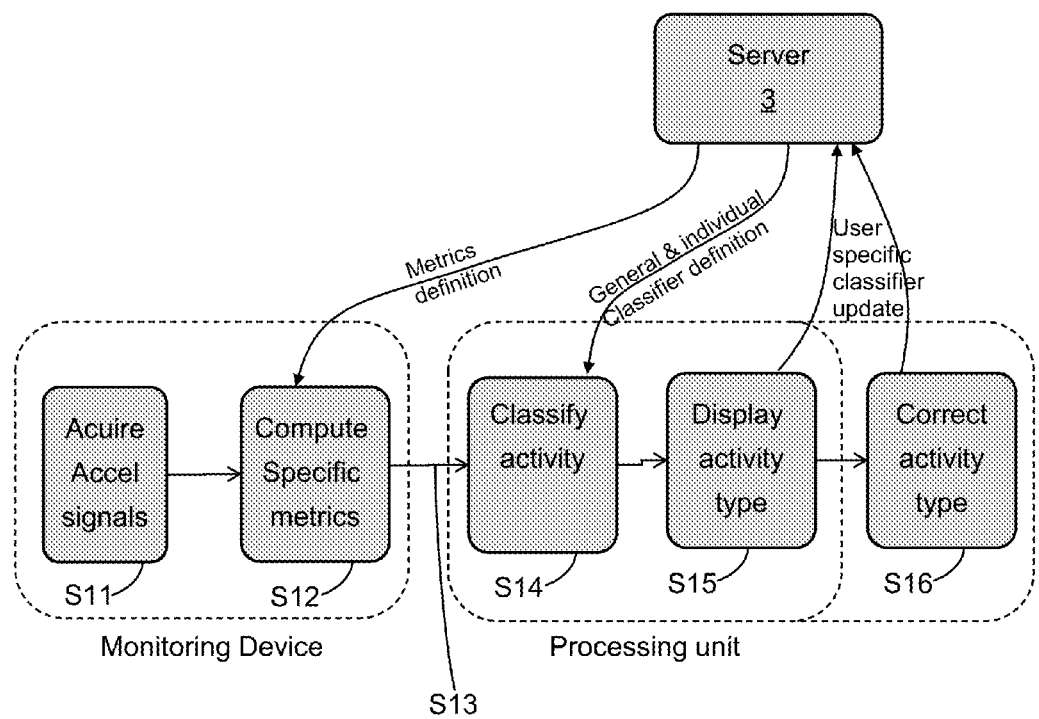
FIG. 4 illustrates the disclosed process enabling to accurately recognise physical activities.

Acceleration signals are for example, sampled at a rate between 10 Hz and 100 Hz, for example 20, 30, 40 or 50 Hz (step S11 in FIG. 4). The sampled signals are inputted, preferably in real time, into a calculation block (digital filter or simple arithmetics) (step S12 in FIG. 4).

It should be noted that for energy savings purposes, when monitoring device is at complete still, the sampling rate can be decreased for a while, and can be returned to the normal sampling rate when a new movement is detected.

As shown in FIG. 5, the sampled acceleration signals are computed over a time unit denoted T1; and at the end of this time unit T1, the complete value of metric M1 is outputted.

Similarly, other metrics M2, M3, M4 are also computed during the same time unit T1. The result of step S12 is a series of N specific metrics values M1V, M2V, M3V, M4V.

Each metric value is a number between 0 and a predefined maximum number MVmax. Advantageously, each metric value is a digital item, which occupies a limited number of bits. This number of bits can be 8, and in this case, each metric value fits in one byte (size=1 byte) and MVmax is 255. This number of bits can be 4, and in this case, each metric value fits in one half-byte and MVmax is 15; this number of bits can be 3, and in this case, and MVmax is 7; this number of bits can also be 2, or 5, or 6, or 7 or more than 8.

It should be noted that the size of each metric can be different; for example, metric M1 can have a one byte size, whereas metric M2 can have a half byte size.

With reference to FIG. 5, at the end of the first time unit T1A, four metrics values are outputted and stored, and then the values of each specific metric counter is reset to 0 for a renewed calculation. The computation resumes for the next time unit T1B. At the end of the second time unit T1B and stored, four metrics values are again outputted, and the values of each specific metric counter is again reset to 0.

The computation resumes for the next time unit T1C. At the end of the third time unit T1C, four metrics values are again outputted and stored, and the values of each specific metric counter is again reset to 0, and so on continuously on next time units T1D, The respective values of each metric (M1V,M2V,M3V, M4V) for each time unit (T1A,T1B,T1C, . . . ) is stored into the memory of the monitoring device which constitute a series of values. There may be provided a timestamp for each time unit (T1A,T1B,T1C, . . . ).

The predefined time unit T1 corresponds to frequency F1, such that F1=1/T1. In the example T1=60s and F1=1/60 Hz. More generally, T1 can be comprised between 10 seconds and 360 seconds. T1 is chosen to minimise a possible loss of relevant data regarding activity if a change of activity occurs within T1. For example, when T1 is 60 second, a possible error on the calculation of the duration of activity is less than one minute.

Whenever possible or at predefined moments, the monitoring device sends out this set of data to the processing unit 2 (arrow S13); for example each time the smartphone 2 and the monitoring device 1 come again in wireless communication, or at a predefined time intervals in case the monitoring device stays in wireless communication with the smartphone.

It should be noted that even if the monitoring device stays out of range of the processing unit for, let's say one hour, the volume of data that needs to be stored and sent out remains very low. There are a seraies of 60 records each with the 4 metrics values, that is to say if metrics have each a one byte size, 240 bytes. Even if the monitoring device stays out of range of the processing unit for 24 h (one full day), if metrics outputted each minute have each a one byte size, this requires 5760 bytes, namely far less than 10 kbytes, a memory size still fairly reasonable among low consumption 3V microcontrollers.

In other embodiments with N=5 and each metrics values fitting in a 3-bit space (2 bytes can store 5 metrics values), the overall data size for one hour storage would be 120 bytes. Therefore, the specific metrics are really small data-size metrics.

Regarding definition of metrics, metric M1 can possibly be the timed-average sum of square values of acceleration signals, which represents the mean energy of the acceleration signals; alternately, M1 can also possibly be based on the jerk signals (derivative of acceleration signals) or cubic values of acceleration signals. Metric M2 can possibly be the statistical variance of acceleration signals over the T1 time period, or a weighted sum of square root of acceleration signals deviation from a given mean value.

Metric M3 can possibly be the number of detected steps over T1, divided by an integer, to fit into MVmax for this metric, M3 can also be a count of positive apexes of a time filtered acceleration signal. Metric M4 can possibly represent the proportion of time over T1, when the acceleration signals are smaller than a predefined threshold; M4 (or M4') can alternately be the proportion of time over T1, when the acceleration signals are greater than another predefined threshold.

If the monitoring device comprises a pressure sensor, one of the metric can optionally represent changes of altitude, if the monitoring device comprises a gyrometer, one of the metric can optionally represent change(s) in orientation.

At the processing unit 2, upon reception of data from the monitoring device 1, there is available a table (also called 'array') of data with N lines and K columns, K representing the number of time units T1$i$ stored; in other words, there are a series of samples (Ki samples) over time, each of N metrics values, as represented in the lower part of FIG. 5.

The processing unit 2 performs the task, for each Ki sample, of identifying the relevant type of activity (step S14 in FIG. 4). This can be done by using reference metrics distributions, as illustrated in FIG. 6.

Figures 7, 8:
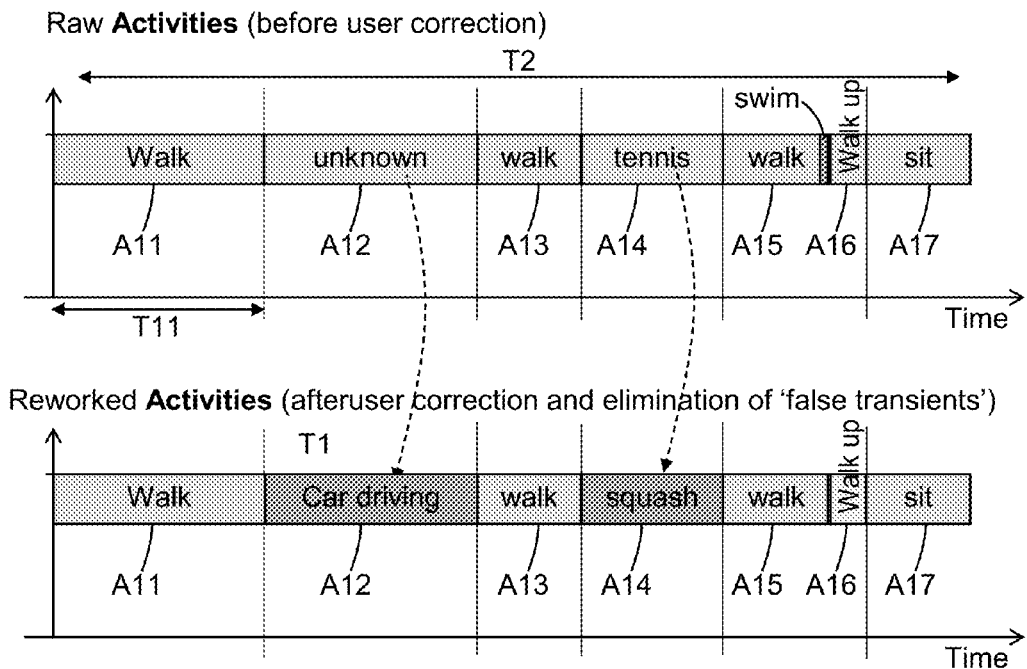
FIG. 7 illustrates a user activity time chart, with user correction.
FIG. 8 illustrates an example of transfer matrix used in an activity classifier.

Each Ki sample can be compared to the reference metrics distributions with a 'nearest neighbour' logic of decision; alternately, a transfer matrix TM can be provided with N columns and J lines, J being the number of activities in the set of predefined activities (see FIG. 8). J can be rather large, at least 15, typically in the range 20-25, not excluding more than 30.

The following matrix computation is performed:

$$R = TM \times Ki \text{ sample,}$$

and the line with the highest score represents the more likely activity type.

Also, the construction of the time evolution of each metric value, like the curves G1-G4 on FIG. 5, can supply additional information to confirm a change of type of activity.

The transfer matrix TM can be a global transfer matrix, i.e. coming from the initial learning phase, but not specific to a particular user U.

The transfer matrix TM can also take into account previous information coming from data already known to this particular user (reinforcement learning), as it will be explained later.

This calculation is done for each Ki sample, and then all the results are concatenated (appended) to form a sequence of activity types as shown in FIG. 7; this allows to display to the user the sequence of activity types A11-A17 presumably performed by the user over a general time period noted T2 (step S15 in FIG. 4).

With the help of this display, the user can confirm or correct partly the type of activity performed over a general time period T2 (step S16 in FIG. 4).

In the shown example, the user corrects the type of activity of the second time segment A12, from 'unknown' to 'car driving', and the user corrects the type of activity of the fourth time segment A14, from 'tennis' to 'squash'.

This is an example of the step /g/ of the method: display the time chart of activity types presumably performed by the first user on the display and allow the user to confirm or correct partly the type of activity performed over the period T2.

If correction was stated by the first user, the processing unit is caused to send a correction information back to the server, which allows to define or refine the user-specific activity classifier.

For example, if the user stated to practice squash instead of tennis, the user specific classifier will be modified such that the parameters of the transfer matrix TM tend to favour squash over tennis.

It should be noted that other correction(s) can be performed without displaying (without asking the user for confirmation). For example, after activity denoted A15, a short swim activity is inferred from the classifier result; however this is probably an error linked to some transient from one activity to another. Therefore, the swim activity is replaced by a walk activity (previous activity).

Also, the curves G1-G4 exhibiting the change over time of each metric can be used to eliminate some inadvertent result of the classifier.

Anyway, when an activity is long enough, the risk of false activity detection is quite low, except if it is a new activity performed by the particular user.

Likewise, the user-specific activity classifier can take into account individual classifiers of the other users having a similar profile. For example a user belonging to the group of female users will more likely practice an aqua-biking activity than a male user. Also groups by age can be provided to adapt the likeliness of some activity to the age of the practitioner.

The relevance of the parameters of the transfer matrix TM can thus be increased. This is be done by amending the parameters included in the transfer matrix TM, according to each user profile (age, gender, height, weight, . . . ).

A way to render the classifier specific to a specific user U is to provide parameterization of the matrix content TM, with coefficients reflecting the user profile.

Another way to enhance activity recognition is to use the historical data stored in the server and to affect a higher likelihood (in other words give 'priority') to the activities already practiced by this particular user (either recognized automatically or declared by the user). This does not prevent the user to practice a new activity, but this may require a correction statement as explained in step /h/ of the method.

One way to do this practically is to parameterize TM to have higher results on lines corresponding to activities already practiced by this particular user.

According to another aspect, the list of activities may be defined by each particular user; this list can even include on or more specific activities that were not part of the initial list of activity defined for the learning phase.

Advantageously, at step /f/, after allocation for each time unit of an activity type, time units are appended in timed array of consistent activities. At the time of a change between two activity types, the processing unit can eliminate some unlikely transients, (e.g. 'swim' at FIG. 7).

Advantageously, the accurate knowledge of the type of activity over time allows to better calculate the caloric burn induced by the all activities performed by the user.

Further, the inventors have found that the present method as disclosed and claimed can also be used advantageously in the special case where the activity monitoring device 1, the processing unit 2 and the display 4 form part of a single device such as a smartphone. In such case, the metrics calculation involves only a very small extra electrical consumption on the smartphone.

The invention claimed is:

1. A method implemented in a system which comprises:
   at least a lightweight personal wearable monitoring device, supplied by a battery, comprising at least an accelerometer which senses acceleration signals,
   a processing unit, a display,
   at least a remote server, said method comprising the steps:

/a/ collecting, from a plurality of individuals caused to practice various physical activities from a set of predefined activities, acceleration data from one or several sensing devices placed on each of said individuals, and at different body positions, /b/ defining N small data-size specific metrics, to be computed from acceleration signals sensed by accelerometer(s) of monitoring devices, which allow to define a global activity classifier, said activity classifier being an algorithm designed to allocate a current activity among the a set of predefined activities, /c/ acquiring, over time, at a first monitoring device worn by a first user, acceleration signals from the accelerometer of the first monitoring device, /d/ calculating, at the first monitoring device, periodically at a predefined rate F1, and over each lapsed time unit (T1=1/F1), specific metrics values from the sensed signals, to form a series of specific metrics values, /e/ send this series of specific metrics values to the processing unit, /f/ at the processing unit, allocate an activity type for each time unit together with corresponding specific metrics values of the received series, to form a time chart of activity types presumably performed by the first user over a second period (T2), /g/ display the time chart of activity types presumably performed by the first user on the display and allow the first user to confirm or correct partly the type of activity performed over the second period (T2), /h/ send a correction information back to the server, which allows to define or refine a user-specific activity classifier.

2. The method according to claim 1, wherein the set of predefined activities comprises at least: normal walk, fast walk, run, dance, climbing stairs, rest, office sit, TV watch, sports like football, swimming, rowing, treadmill run, biking, skiing, skating.

3. The method according to claim 1, wherein the number of specific metrics N is no greater than 8, wherein each metric has a size no greater than 8 Bits.

4. The method according to claim 1, wherein the number of specific metrics N is equal to 5, wherein each metric has a size less than 5 Bits.

5. The method according to claim 1, wherein each metric is computed at an end of every predefined time unit (T1) with the acceleration data sensed over the lapsed predefined time unit, said time unit having a duration comprised between 10 seconds and 360 seconds.

6. The method according to claim 1, in which the processing unit and the display form part of a smartphone.

7. The method according to claim 1, in which at step /f/, at the processing unit, the allocation of type activity relies on a transfer matrix TM computation.

8. The method according to claim 1, in which at step /f/, at the processing unit, the allocation of type activity relies on the classifier resulting from the global classifier and the user-specific activity classifier, incrementally amended through parameterization with the user feedbacks.

9. The method according to claim 1, in which at step /f/, it further comprises:
Append time units in timed series of consistent activities, with elimination of unlikely transients.

10. The method according to claim 1, in which the activity monitoring device has a low battery capacity, namely less than 100 mAh and a good battery autonomy namely no less than 2 weeks.

11. The method according to claim 1, in which the activity monitoring device, the processing unit and the display form part of a single device such as a smartphone.

12. A system comprising:
at least a lightweight personal wearable monitoring device,
a processing unit, a display,
at least a remote server,
the system being configured to carry out the steps of:

/a/ collecting, from a plurality of individuals caused to practice various physical activities from a set of predefined activities, acceleration data from one or several sensing devices placed on each of said individuals, and at different body positions, /b/ defining N small data-size specific metrics, to be computed from acceleration signals sensed by accelerometers of monitoring devices, which allow to define a global activity classifier, /c/ acquiring, over time, at a first monitoring device worn by a first user, acceleration signals from the accelerometer of the first monitoring device, /d/ calculating, at the first monitoring device, periodically at a predefined rate F1, and over each lapsed time unit, specific metrics values from the sensed signals, to form a series of specific metrics values, /e/ send this series of specific metrics values to the processing unit, /f/ at the processing unit, allocate an activity type for each time unit together with corresponding specific metrics values of the received series, to form a time chart of activity types presumably performed by the first user over a second period, /g/ display the time chart of activity types presumably performed by the first user on the display and allow the first user to confirm or correct partly the type of activity performed over the second period, /h/ send a correction information back to the server, which allows to define or refine a user-specific activity classifier.

* * * * *